US012740936B2

(12) United States Patent
Lin et al.

(10) Patent No.: US 12,740,936 B2
(45) Date of Patent: Sep. 22, 2026

(54) METHOD FOR IMPROVING SKIN COMPLEXION BY USING ROSA CANINA EXTRACT

(71) Applicant: TCI CO., LTD., Taipei (TW)

(72) Inventors: Yung-Hsiang Lin, Taipei (TW); Hsiao-Nai Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 293 days.

(21) Appl. No.: 18/518,455

(22) Filed: Nov. 23, 2023

(65) Prior Publication Data

US 2024/0180814 A1 Jun. 6, 2024

Related U.S. Application Data

(60) Provisional application No. 63/386,173, filed on Dec. 6, 2022.

(30) Foreign Application Priority Data

Sep. 15, 2023 (TW) ................................ 112135413

(51) Int. Cl.
*A61K 8/9789* (2017.01)
*A61Q 19/00* (2006.01)

(52) U.S. Cl.
CPC ............ *A61K 8/9789* (2017.08); *A61Q 19/00* (2013.01)

(58) Field of Classification Search
CPC ................................ A61K 8/978; A61Q 19/00
See application file for complete search history.

(56) References Cited

U.S. PATENT DOCUMENTS

| | | | | |
|---|---|---|---|---|
| 11,877,998 | B2 * | 1/2024 | Torok | A23L 33/16 |
| 2021/0369595 | A1 * | 12/2021 | Pecher | A61K 8/06 |

FOREIGN PATENT DOCUMENTS

| | | | | |
|---|---|---|---|---|
| CN | 111135124 A | * 5/2020 | | A61K 8/602 |
| CN | 112312889 A | * 2/2021 | | A61Q 19/08 |
| KR | 2020050247 A | * 5/2020 | | A61K 31/405 |

OTHER PUBLICATIONS

Gao Z, et al, KR 2020050247 A, machine translation, 4 pages (Year: 2020).*
CN-112312889-A English translation PDF copy (Year: 2021).*
Why is the rosehip, which has made a big name in the beauty industry, so rarely seen?—HanBenLife, Nov. 15, 2017, < https://mp.weixin.qq.com/s?_biz=MzlwMDM4MDY1Mg==&mid=2650074009&idx=2&sn=7be1a51af917119cef2173405ba33dce&chksm=8f48482371b0a1b6eaf3ebc38b88a5e17fabf0e88d35fcd1f89deeaac2263534a8a9405243fd#rd > pp. 3-4.
<The Benefits and Effects of Rosehips Rosehip Brewing Method,>http://www.huachapu.com/huacha/qiangwei.shtml, Oct. 22, 2013 Full text.
Chuck Huang, Rosehips,<https://helloyishi.com.tw/herbal-alternatives/herbals/rose-hips#google_vignette,>Aug. 25, 2020 Full text.
Rosehips, Samsangtong Wellnessflowertea,<https://www.samsangtong.com.hk/products/%E4%B8%89%E7%94%9F%E5%A0%82%E9%A4%8A%E7%94%9F%E8%8A%B1%E8%8C%B6%E4%B8%AD%E8%97%A5%E6%9D%90-%E7%8E%AB%E7%91%B0%E6%9E%9C,>Apr. 22, 2018 Full text.

* cited by examiner

*Primary Examiner* — Anand U Desai
(74) *Attorney, Agent, or Firm* — Chieh-Mei Wang

(57) ABSTRACT

A method for improving skin complexion of a subject in need thereof is provided. The method includes: administering to the subject an effective dose of a *Rosa canina* extract. The *Rosa canina* extract is obtained by extracting a whole fruit of *Rosa canina* by water. The *Rosa canina* extract achieves the effect of improving skin complexion by promoting iron absorption by cells, promoting hemoglobin concentration, promoting blood iron content, promoting mitochondrial activity in cells, promoting elastin content in skin cells, enhancing antioxidant capacity of skin, and enhancing expression levels of SOD3, SIRT1 and NADSYN genes in skin fibroblasts.

6 Claims, 9 Drawing Sheets
(1 of 9 Drawing Sheet(s) Filed in Color)

Specification includes a Sequence Listing.

Experimental group

Blank group

METHOD FOR IMPROVING SKIN COMPLEXION BY USING ROSA CANINA EXTRACT

CROSS-REFERENCES TO RELATED APPLICATIONS

This application claims the benefit of U.S. provisional application Ser. No. 63/386,173, filed on Dec. 6, 2022, and claims priority to patent application No. 112135413, filed in Taiwan, R.O.C. on Sep. 15, 2023. The entirety of the above-mentioned patent applications are hereby incorporated by references herein and made a part of the specification.

REFERENCE OF AN ELECTRONIC SEQUENCE LISTING

The contents of the electronic sequence listing (P223935USI.xml; Size: 6,505 bytes; and Date of Creation: Oct. 27, 2023) is herein incorporated by reference in its entirety.

BACKGROUND

Technical Field

The present disclosure relates to usage of a *Rosa canina* extract, and particularly relates to use of a *Rosa canina* extract in preparation of a composition for improving skin complexion to a subject in need thereof.

Related Art

Modern people often suffer from poor complexion and lack of vitality because of their different diets and daily routines. “Prevention is better than cure” is an ideal state of modern people, and the use of natural food to regulate the health condition has always been the direction of all people’s efforts.

The *Rosa canina* is not the fruit of the rose as it is commonly known, but is the red fruit of the *Rosa canina* plant. The red *Rosa canina* is often used in the form of *Rosa canina* oil.

SUMMARY

In view of this, in order to further seek new use of *Rosa canina*, a *Rosa canina* extract may be applied to preparation of a composition for improving skin complexion to a subject in need thereof.

In some examples, the *Rosa canina* extract is used for promoting iron absorption by cells.

In some examples, the *Rosa canina* extract is used for promoting hemoglobin concentration.

In some examples, the *Rosa canina* extract is used for promoting blood iron content.

In some examples, the *Rosa canina* extract is used for promoting mitochondrial activity in cells.

In some examples, the *Rosa canina* extract is used for promoting elastin content in skin cells.

In some examples, the *Rosa canina* extract is used for enhancing antioxidant capacity of skin.

In some examples, the *Rosa canina* extract is used for enhancing expression levels of SOD3, SIRT1 and NADSYN genes in skin fibroblasts.

In some examples, the *Rosa canina* extract is used for reducing skin pore size.

In some examples, an effective dose of the *Rosa canina* extract is 4 g/day.

Based on the above, the *Rosa canina* extract according to any example can be used for preparing a composition for improving skin complexion to a subject in need thereof. The *Rosa canina* extract according to any example can be used for promoting iron absorption by cells, promoting a hemoglobin concentration, promoting an iron content in blood, promoting a mitochondrial activity in cells, promoting an elastin content in skin cells, enhancing an antioxidant capacity of skin, and enhancing expression levels of SOD3, SIRT1 and NADSYN genes in skin fibroblasts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
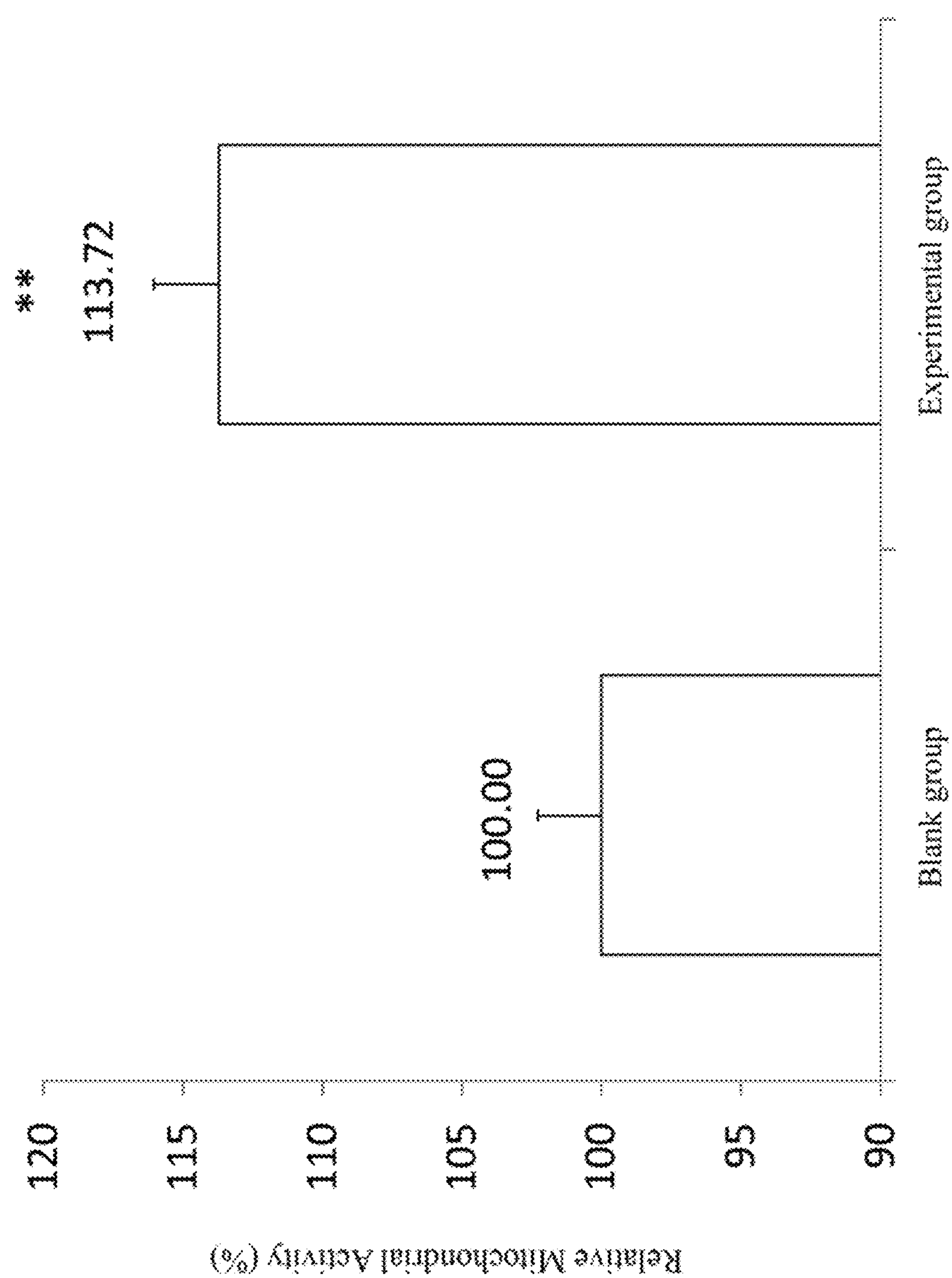
FIG. 1 is a graph showing results of a relative mitochondrial activity test.

As used herein, the term “extract” refers to a product prepared by extraction. The extract can be present as a solution dissolved in a solvent, or the extract can be present as a concentrate or essence without or substantially without a solvent. As used herein, the term “subject” refers to an organism in need, such as a human.

The “*Rosa canina*” as used herein refers to the whole fruit of *Rosa canina* L, also known as rose hips. In some examples, the *Rosa canina* may be fresh *Rosa canina*, dried *Rosa canina* or frozen *Rosa canina*. In some examples, drying may be air drying, sun drying, shade drying or freeze drying. In some examples, the *Rosa canina* may further include the fruit that is whole, chopped, diced, milled, ground, or otherwise processed to affect the size and physical integrity of the raw material. In some examples, the *Rosa canina* is *Rosa canina* produced in Chile.

In some examples, the *Rosa canina* extract is a *Rosa canina* extraction solution prepared by water extraction. Here, the water extraction includes: by using water as a solvent, after the *Rosa canina* and water are mixed, the mixture is processed at a specific temperature for a specific time to obtain the *Rosa canina* extraction solution.

In some examples, the specific temperature is 90° C. to 80° C. In an example, the specific temperature is 85±5° C. In an example, the specific temperature is 85° C. In some examples, the specific time is 50 min to 80 min. In some examples, the specific time is 60 min.

In some examples, "for a special time" means that after 60 min, when a Brix value of the *Rosa canina* extraction solution is 5±0.5° Bx (Degrees Brix), the *Rosa canina* extract is obtained. In some examples, if the Brix value is less than 4.5° Bx, the extraction is carried out for another 30 min. That is, the *Rosa canina* extract is obtained when the Brix value of the *Rosa canina* extraction solution reaches the acceptance criterion 5±0.5° Bx.

In some examples, in the water extraction, a weight ratio of water to *Rosa canina* is (15 to 5):1. For example, the ratio water to *Rosa canina* is 10:1. Here, if the amount of the solvent is too small or the specific time is too short, the extraction efficiency will be significantly reduced. If the specific time is too long, degradation of active ingredients in the extract may occur.

In some examples, the *Rosa canina* extract is the *Rosa canina* extract prepared by water extraction and filtration. The filtration means that the *Rosa canina* extraction solution obtained after the water extraction is filtered by means of a screen or centrifugation, so as to remove solids in the *Rosa canina* extraction solution. For example, the *Rosa canina* extraction solution is filtered through a 400 mesh screen to obtain the *Rosa canina* extract.

In some examples, an effective dose of the *Rosa canina* extract is 4 g/day.

In some examples, the present disclosure provides a use of the *Rosa canina* extract in preparation of a composition for improving skin complexion to a subject in need thereof. Here, the improvement of skin complexion of a subject in need thereof can be achieved by at least one uses in promoting iron absorption by cells, promoting a hemoglobin concentration, promoting an iron content in blood, promoting a mitochondrial activity in cells, promoting an elastin content in skin cells, enhancing an antioxidant capacity of skin, and enhancing expression levels of SOD3, SIRT1 and NADSYN genes in skin fibroblasts. Here, the improvement of skin complexion can be expressed in the appearance of the subject in need thereof through visual perception. For example, the lip color or pale face turns ruddy, the dull skin turns bright, and the sagging skin turns elastic or lustrous.

In some examples, the *Rosa canina* extract is used for promoting a mitochondrial activity in cells. Here, the accumulation of JC-1 is a marker of mitochondrial activity. In healthy mitochondria with normal membrane potential, JC-1 exists in the form of a polymer. When the membrane potential of mitochondria decreases, JC-1 will become a monomer. As a result, JC-1 can be used as a marker for evaluating mitochondrial activity. Mitochondria are the energy manufacturing factory of cells, and the mitochondrial activity will decrease due to damage of the external environment. If the mitochondrial activity can be promoted, the metabolic rate and repair of cells can be promoted, so that the subject can have better complexion.

In some examples, the *Rosa canina* extract is used for promoting an elastin content in skin fibroblasts. Here, the increase of the elastin content is beneficial to maintain the elasticity of epidermis, so that the subject can have better complexion.

In some examples, the *Rosa canina* extract is used for inhibiting a content of reactive oxygen species (ROS) in skin fibroblasts. In other words, the *Rosa canina* extract serves as a scavenger of ROS. That is, by reducing the content of ROS in cells, the oxidative damage of cells caused by ROS is reduced.

In some examples, the *Rosa canina* extract is used for enhancing expression levels of SOD3, SIRT1 and NADSYN genes in skin fibroblasts. The expression of the SOD3 (superoxide dismutase 3) gene can promote cells to produce superoxide dismutase. The expression of the SIRT1 (NAD-dependent deacetylase sirtuin-1) gene can reduce DNA damage of cells, protein inactivation and inflammatory reaction. The NADSYN gene (glutamine-dependent $NAD^+$ synthesis) helps cells to synthesize NAD, so as to provide an energy source for mitochondria and maintain viability.

In some examples, the *Rosa canina* extract is used for promoting absorption of iron by intestinal cells. In some examples, the *Rosa canina* extract is used for promoting a hemoglobin concentration. In some examples, the *Rosa canina* extract is used for promoting an increase of an iron content in blood. Here, iron is a very important mineral in the human body. Iron and hemoglobin help transport oxygen throughout the body, making it easier for cells to obtain oxygen and contributing to improvement of skin complexion.

In some examples, the composition is a food composition, and the composition includes at least an effective content of the *Rosa canina* extract. In some examples, the effective content of the *Rosa canina* extract is 4 g/day.

In some examples, the composition may be a pharmaceutical composition. In other words, the pharmaceutical composition includes an effective content of the *Rosa canina* extract. In some examples, the effective content of the *Rosa canina* extract is 4 g/day.

In some examples, the pharmaceutical composition can be made into an enterally or orally administered dosage form by using techniques well known to those skilled in the art. These enterally or orally administered dosage forms include, but not limited to, tablets, troches, lozenges, pills, capsules, dispersible powders or granules, solutions, suspensions, emulsions, syrups, elixirs, slurries and the like.

In some examples, the pharmaceutical composition can be made into a parenterally or topically administered dosage form by using techniques well known to those skilled in the art. These parenterally or topically administered dosage forms include, but not limited to, injections, sterile powders, external preparations and the like. In some examples, the pharmaceutical composition may be administered by one of the parenteral routes selected from the group consisting of subcutaneous injection, intraepidermal injection, intradermal injection or intralesional injection.

In some examples, the pharmaceutical composition may further include a pharmaceutically acceptable carrier widely used in pharmaceutical manufacturing techniques. For example, the pharmaceutically acceptable carrier may include be one or more of the following agents: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome and the like. The selection and quantity of these agents are within the professional quality and routine skill of those skilled in the art.

In some examples, the pharmaceutically acceptable carrier includes a solvent selected from the group consisting of water, normal saline, phosphate buffered saline (PBS) and an aqueous solution containing alcohol.

In some examples, the composition may be an edible composition for non-medical purposes. In some examples, the edible composition can be made into a food product or can be a food additive. That is, the edible composition can be added by a conventional method during the preparation of food ingredients to obtain a food product, or added during the manufacturing of the food product. Here, the food product may be a product prepared with edible materials for humans or animals to eat. In some examples, the edible composition further includes the food itself.

In some examples, the food product may be, but not limited to, beverages, fermented foods, bakery products, health foods for non-medical purposes or dietary supplements for non-medical purposes.

Example 1: Preparation of Test Sample

A whole fruit of *Rosa canina* (frozen fresh *Rosa canina* produced in Chile) and water were mixed in a weight ratio of 1:10. The mixture was held at 85° C. for 1 h to obtain a primary extraction solution. Then, the primary extraction solution was filtered through a 400 mesh screen to remove solids, thereby obtaining a *Rosa canina* extract. Here, the Brix value of the *Rosa canina* extraction solution was equal to or greater than 5° Bx.

Example 2: Mitochondrial Activity Test 2-1 Materials and Instruments:

Cell line: human skin fibroblasts CCD-966sk (BCRC No. 60153), hereinafter referred to as skin fibroblasts.

Cell culture medium: minimum essential medium (MEM, purchased from Gibco, Catalog No. 11095080) containing 10 vol % of FBS (purchased from Gibco, Catalog No. 10437-028), with additional ingredients to make it contain 1 mM sodium pyruvate (purchased from Gibco, Catalog No. 11360-070), 1.5 g/L sodium bicarbonate (purchased from Sigma, Catalog No. S5761-500G) and 0.1 mM non-essential amino acid solution (purchased from Gibco, Catalog No. 11140050).

Buffered saline solution (DPBS solution): purchased from Gibco, Catalog No. 14200-75.

Trypsin: 10× Trypsin-EDTA (purchased from Gibco, Catalog No. 15400-054).

Mitochondrial membrane potential assay kit (BD MitoScreen (JC-1) kit, Model BDB551302). The mitochondrial membrane potential assay kit has a JC-1 dye (freeze-dried) and a 10× analysis buffer. Before use, the 10× analysis buffer was diluted 10-fold with 1×PBS to form a 1× analysis buffer. 130 μL of DMSO was added to the JC-1 dye (freeze-dried) to form a JC-1 stock solution. Then, the JC-1 stock solution was diluted with the 1× analysis buffer to form a JC-1 working solution (JC-1 mitochondria-specific dye). A ratio of the JC-1 stock solution to the 1× analysis buffer was 1:100.

Flow cytometry: purchased from BD Pharmingen, Model BD™ Accuri C6 Plus.

2-2 Test Procedure:

The skin fibroblasts were inoculated into a 6-well culture plate containing 2 mL of cell culture medium per well at a density of $1\times10^5$ cells per well, and cultured in a $CO_2$ incubator for 24 h.

The culture medium in each well of the culture plate was replaced with 2 mL of test medium. The test medium of the experimental group was a cell culture medium containing 0.125% (m/v) of *Rosa canina* extract prepared in Example 1. The test medium in the blank group was a simple cell culture medium (without the *Rosa canina* extract). The culture plate was placed in an environment containing 5% $CO_2$ at 37° C., and the skin fibroblasts were cultured for 24 h.

The test medium was removed from the culture plate, and the culture plate was rinsed with 1 mL of 1×PBS solution for 2 times. 200 μL of trypsin was added to each well, and the reaction was carried out in the dark for 5 min. After the reaction, the cell culture medium was added to terminate the reaction. The cells and the cell culture medium in each well were collected to the corresponding 1.5 mL centrifuge tube, and the centrifuge tubes containing the cells and the cell culture medium were centrifuged at 400×g for 10 min.

The supernatant was removed, and the cell precipitate was redissolved with 1 mL of 1×PBS solution or transferred to a 15 mL centrifuge tube to form a cell suspension. The centrifuge tube containing the cell suspension was centrifuged at 400×g for 5 min.

After the centrifugation, the supernatant in each centrifuge tube was removed, and 100 μL of JC-1 working solution was added to each centrifuge tube. The cell precipitate in each centrifuge tube and the JC-1 working solution in each centrifuge tube were vortexed uniformly and cultured in the dark for 15 min. After 15 min, each centrifuge tube was centrifuged at 400×g for 5 min.

After the centrifugation, the supernatant in each centrifuge tube was removed, and the cell precipitate in each tube was redissolved with 1 ml of 1×PBS solution. The cell suspension was centrifuged at 400×g for 5 min. After the centrifugation, the supernatant in each centrifuge tube was removed, and the cell precipitate in each centrifuge tube was redissolved with 1 ml of 1×PBS solution. The cell suspension was centrifuged at 400×g for 5 min. After the centrifugation, the supernatant in each centrifuge tube was removed, and the cells were resuspended with 500 μL of 1×PBS to obtain the cell suspension to be tested.

A mitochondrial membrane potential in the cell suspension to be tested in each well was measured with the flow cytometry so as to perform mitochondrial activity analysis. The experiments for each group were carried out in triplicate. The results of the triplicate experiments were averaged to obtain a mean. Then, taking the mean of the blank group as 100% relative mitochondrial activity (JC-1 accumulation), the mean of the experimental group was converted into the relative mitochondrial activity (JC-1 accumulation), as shown in FIG. 1.

2-3 Test Results:

The results were subjected to student t-test with software Excel to determine whether there were statistically significant differences between the two sample groups, as shown in FIG. 1. "*" represents a p-value of less than 0.05, "" represents a p-value of less than 0.01, and "*" represents a p-value of less than 0.001. The more "*", the more statistically significant the difference relative to the blank group.

FIG. 1 is a comparative histogram of relative mitochondrial activity of the experimental group treated with the *Rosa canina* extract and the blank group not treated with the *Rosa canina* extract. As shown in FIG. 1, the relative mitochondrial activity of the experimental group was 113.72%. In other words, compared with the blank group, the mitochondrial activity of skin fibroblasts of the experimental group was enhanced by 13.72%. This indicated that the *Rosa canina* extract can enhance the mitochondrial activity of skin fibroblasts.

Example 3: Test for Promotion of Elastin Production 3-1 Materials and Instruments:

Cell line: human skin fibroblasts CCD-966sk (BCRC No. 60153), hereinafter referred to as skin fibroblasts.

Cell culture medium: minimum essential medium containing 10 vol % of fetal bovine serum (FBS; Brand: Gibco). The minimum essential medium was Eagle's minimum essential medium (MEM, purchased from Gibco, Catalog No. 15188-319), with additional ingredients to make it contain 1 mM sodium pyruvate (Brand: Gibco), 1.5 g/L sodium bicarbonate (purchased from Sigma, Catalog No. S5761-500G) and 0.1 mM non-essential amino acid solution (purchased from Gibco).

3-2 Test Procedure:

The skin fibroblasts were inoculated into a 6-well culture plate containing 2 mL of cell culture medium per well at a density of $1\times10^5$ cells per well. The culture plate was placed in an environment containing 5% $CO_2$ at 37° C., and the skin fibroblasts were cultured for 24 h.

The culture medium in each well of the culture plate was replaced with 2 mL of test medium. The test medium of the experimental group was a cell culture medium containing 0.125% (m/v) of *Rosa canina* extract prepared in Example 1. The test medium in the blank group was a simple cell culture medium (without the *Rosa canina* extract). The culture plate was placed in an environment containing 5% $CO_2$ at 37° C., and the skin fibroblasts were cultured for 24 h.

Next, the skin fibroblasts in each group were treated with Fastin™ Elastin Assay kit (Brand: Biocolor), and tested for their elastin production with a full-spectrum spectrophotometer (Brand: BioTek, Epoch). Here, the experiments for each group were carried out in triplicate. The mean of the results of the triplicate experiments was rounded to obtain the elastin production.

Figure 2:
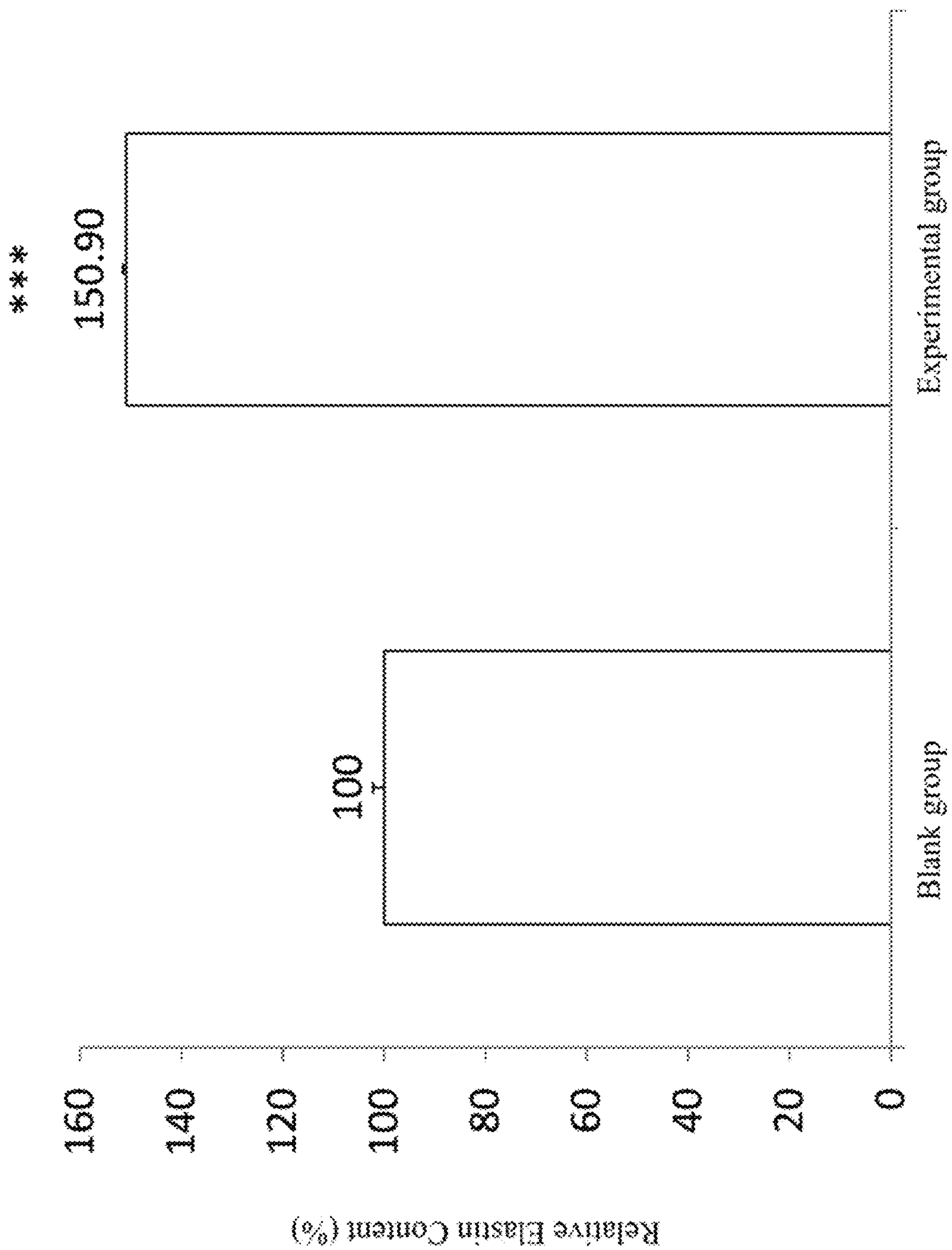
FIG. 2 is a graph showing results of a relative elastin content test.

3-3 Test Results:

Here, the elastin content measured in the blank group was regarded as 100% (i.e., the relative elastin production was 100%), and the elastin content measured in the experimental group was correspondingly converted into the elastin production expressed in %, as shown in FIG. 2. In FIG. 2, "*" represents a p-value of less than 0.05, "" represents a p-value of less than 0.01, and "*" represents a p-value of less than 0.001. The more "*", the more statistically significant the difference.

Referring to FIG. 2, based on the case that the elastin production of the blank group was 100%, the elastin production of the experimental group was 150.9%. The elastin production of the experimental group was significantly was enhanced by 50.9%, indicating that the skin fibroblasts treated with the *Rosa canina* extract for 24 h could product more elastin. Thereby, the skin fibroblasts have the function of promoting synthesis of elastin in skin cells. After taken by a subject in need thereof, the *Rosa canina* extract can promote synthesis of elastin in skin cells of the subject, thereby improving the skin elasticity of the subject.

Example 4: Test for Inhibition of ROG Production

Here, a fluorescent probe DCFH-DA was used in combination flow cytometry to measure the change of an ROS content in human skin fibroblasts CCD-966sk after being treated with the *Rosa canina* extract of the present disclosure.

4-1 Materials and Instruments:

Cell line: Human skin fibroblasts CCD-966sk from Bioresource Collection and Research Center (BCRC; Catalog No. 60153), hereinafter referred to as skin fibroblasts.

Cell culture medium: minimum essential medium (MEM, purchased from Gibco, Catalog No. 11095080) containing 10 vol % of FBS (purchased from Gibco, Catalog No. 10437-028), with additional ingredients to make it contain 1 mM sodium pyruvate (purchased from Gibco, Catalog No. 11360-070), 1.5 g/L sodium bicarbonate (purchased from Sigma, Catalog No. S5761-500G) and 0.1 mM non-essential amino acid solution (purchased from Gibco, Catalog No. 11140050).

Phosphate buffered saline solution (PBS solution): purchased from Gibco, Catalog No. 10437-028.

DCFH-DA solution: 2,7-dichloro-dihydro-fluorescein diacetate (DCFH-DA, Catalog No. SI-D6883, purchased from Sigma) was dissolved in dimethyl sulfoxide (DMSO, purchased from Sigma, Catalog No. SI-D6883-50 MG) to obtain the 5 mg/ml DCFH-DA solution.

Flow cytometry, BD Accuri C6 Plus

Hydrogen peroxide solution ($H_2O_2$): purchased from Sigma-Aldrich, Catalog No. 95299-1L.

Trypsin (Trypsin-EDTA): 10× Trypsin-EDTA (purchased from Gibco, Catalog No. 15400-054) diluted 10-fold with 1×PBS solution.

4-2 Test Procedure:

The skin fibroblasts were inoculated into a 6-well culture plate containing 2 mL of culture medium per well at a density of $1\times10^5$ cells per well. The culture plate was placed in an environment containing 5% $CO_2$ at 37° C., and the skin fibroblasts were cultured for 24 h.

After the original cell culture medium was removed, 2 mL of test medium was added to each well of the culture plate, and the skin fibroblasts were cultured at 37° C. for 1 h. The test medium of the experimental group was a cell culture medium containing 0.125% (m/v) of *Rosa canina* extract prepared in Example 1. The test medium in the blank group and the control group was a simple cell culture medium (without the *Rosa canina* extract).

2 μL of 5 μg/mL DCFH-DA solution was added to the cell culture medium in each well, and the cells were treated with the DCFH-DA for 15 min. After the treatment with the DCFH-DA, $H_2O_2$ was respectively added to the experimental group and the control group, and the reaction was carried out at 37° C. for 1 h. Specifically, a 35 wt % hydrogen peroxide solution was first diluted to a concentration of 100 mM (990 μL of redistilled water was added to 10 μL of hydrogen peroxide solution), and then 20 μL of 100 mM hydrogen peroxide solution was added to the 2 mL cell culture plate.

After the reaction, each well was rinsed with 1 mL of 1×PBS solution for 2 times. 200 μL of trypsin was added to each well, and the reaction was carried out in the dark for 5 min. After the reaction, 6 mL of cell culture medium was added to terminate the reaction. The cells and the cell culture medium in each well were collected to the corresponding 1.5 mL centrifuge tube, and the centrifuge tubes containing the cells and the culture medium were centrifuged at 400×g for 10 min.

After the centrifugation, the supernatant was removed, and the cell precipitate was redissolved with a 1×PBS solution. The centrifuge tube was centrifuged at 400×g for 10 min. After the centrifugation, the supernatant was removed, and the cells were resuspended with 1 mL of 1×PBS solution to obtain the cell suspension to be tested.

A fluorescence signal of DCFH-DA in the cell suspension to be tested in each well was detected by flow cytometry. The excitation wavelength for fluorescence detection was 450 to 490 nm, and the emission wavelength was 510 to 550 nm. The DCFH-DA entering the cells was first hydrolyzed into DCFH, and then the DCFH was oxidized by ROS into DCF (dichlorofluorescein). The fluorescence intensity of cells treated with DCFH-DA could reflect the ROS content in cells, thereby obtaining the proportion of the number of cells with high expression of ROS in cells to the number of the original cells. The tests for each group was carried out in triplicate. The results of the triplicate experiments for each group were averaged to obtain a mean. Then, taking the mean of the blank group as 100% relative ROS production, the mean of the control group and the experimental group was converted into the relative ROS production, as shown in FIG. 3.

That is, the experimental group (the group with the *Rosa canina* extract and treated with the hydrogen peroxide solution), the blank group (the group without the *Rosa canina* extract and not treated with the hydrogen peroxide solution), and the control group (the group without the *Rosa canina* extract and treated with the hydrogen peroxide solution) were respectively subjected to experiments in triplicate.

Figure 3:
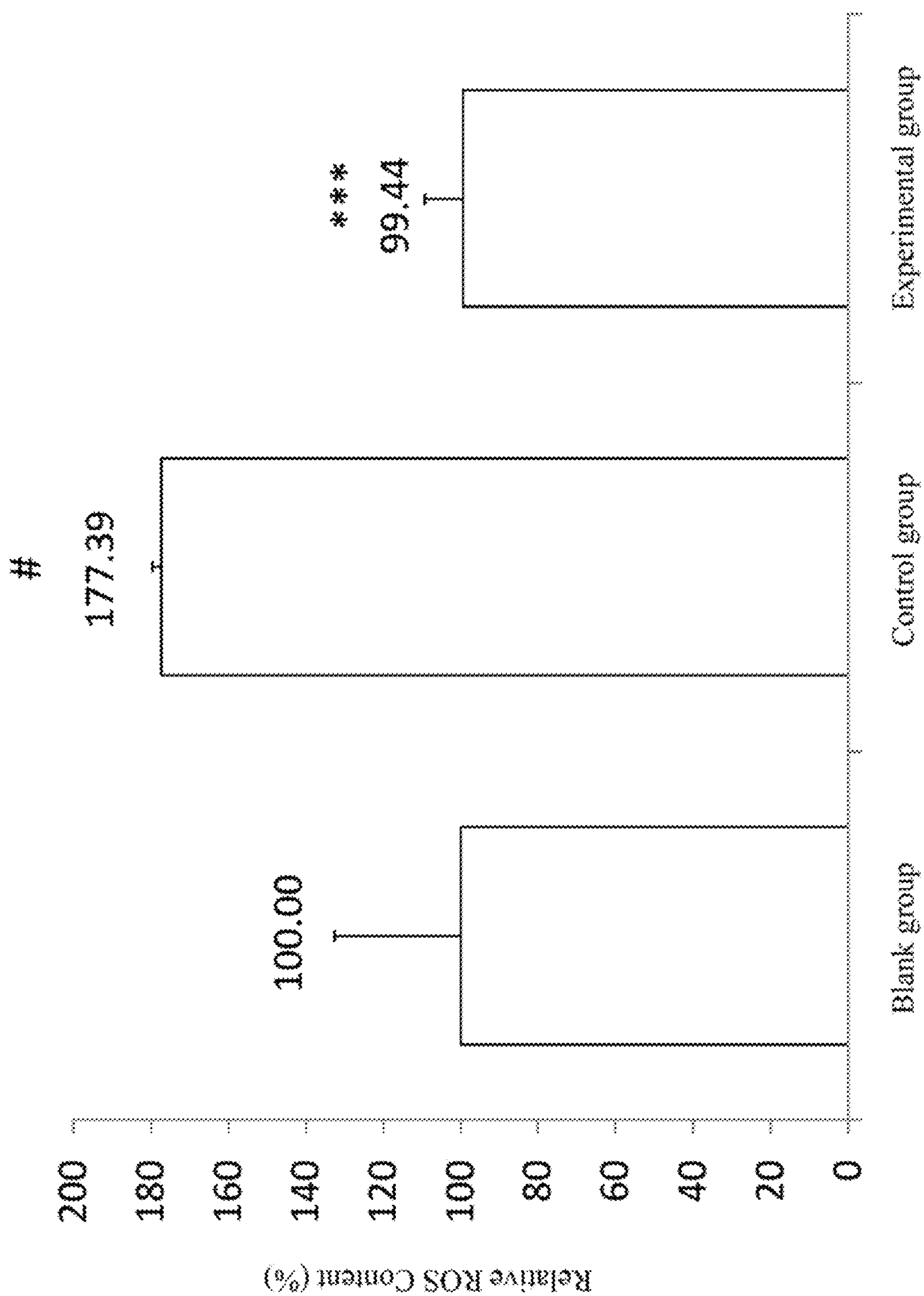
FIG. 3 is a graph showing results of a relative ROS content test.

4-3 Experimental Results:

Here, the ROS content measured in the blank group was regarded as 100% (i.e., the relative ROS content was 100%), and the ROS contents measured in the control group and the experimental group were correspondingly converted into the ROS contents expressed in %, as shown in FIG. 3. In FIG. 3, the results were subjected to student t-test with software Excel to determine whether there were statistically significant differences between the two sample groups. Compared with the control group, "*" represents a p-value of less than 0.05, represents a p-value of less than 0.01, and "***" represents a p-value of less than 0.001. Compared with the blank group, "#" represents a p-value of less than 0.05, "##" represents a p-value of less than 0.01, and "###" represents a p-value of less than 0.001. The more "*" or "#", the more statistically significant the difference.

As shown in FIG. 3, by comparing the results of the blank group and the control group, it can be known that after the treatment with the hydrogen peroxide solution, the relative ROS production (high fluorescence) was greatly increased (about 77.39%, which is statistically significant), which indicated that the treatment with the hydrogen peroxide solution indeed led to the production of ROS in cells, thereby causing serious damage to skin fibroblasts.

On the other hand, by comparing the results of the control group and the experimental group, it can be known that after the cells were treated with the *Rosa canina* extract, the relative ROS production was significantly reduced by about 77.95% (177.39% to 99.44%), which was even lower than that of the blank group. This indicated that the *Rosa canina* extract can effectively reduce the production or accumulation of ROS in cells. In other words, the *Rosa canina* extract may serve as a scavenger of ROS. That is, by reducing the content of ROS in cells, the *Rosa canina* extract can reduce the oxidative damage of cells caused by ROS.

Example 5: Test for Expression Levels of Genes in Cells

Here, the genes to be tested include SIRT1 (Gene ID: 23411), NADSYN (Gene ID: 55191) and SOD3 (Gene ID: 6649).

5-1 Materials and Instruments:

Cell line: Human skin fibroblasts CCD-966sk from Bioresource Collection and Research Center (BCRC; Catalog No. 60153), hereinafter referred to as skin fibroblasts.

Cell culture medium: minimum essential medium (MEM, purchased from Gibco, Catalog No. 11095080) containing 10 vol % of FBS (purchased from Gibco, Catalog No. 10437-028), with additional ingredients to make it contain 1 mM sodium pyruvate (purchased from Gibco, Catalog No. 11360-070), 1.5 g/L sodium bicarbonate (purchased from Sigma, Catalog No. S5761-500G) and 0.1 mM non-essential amino acid solution (purchased from Gibco, Catalog No. 11140050).

5-2 Test Procedure:

First, the skin fibroblasts were inoculated into a 6-well cell culture plate containing 2 mL of cell culture medium per well at a density of $1\times10^6$ cells, and cultured at 37° C. for 24 h.

The skin fibroblasts were divided into an experimental group and a blank group. The cell culture medium of each group was removed and replaced with 2 mL of test medium per well. Then, the culture plate was placed at 37° C., and the skin fibroblasts were cultured for 24 h. The test medium of the experimental group was a cell culture medium containing 0.125% (m/v) of *Rosa canina* extract prepared in Example 1. The test medium in the blank group was a simple cell culture medium.

The skin fibroblasts of each group were collected, and treated with an RNA extraction reagent kit (purchased from Geneaid, Taiwan, Lot No. FC24015-G) to extract RNA for each group. Next, taking 1000 ng of RNA as a template for each group, the RNA was converted into the corresponding cDNA via reverse transcription by using SuperScript® III reverse transcriptase (purchased from Invitrogene, USA, Catalog No. 18080-051). Then, by using ABI StepOnePlus™ Real-Time PCR system (Thermo Fisher Scientific, USA), KAPA SYBR FAST (purchased from Sigma, USA, No. 38220000000) and primers (SEQ ID NO: 1 to SEQ ID NO: 6) in Table 1, the cDNA of each group was subjected to a quantitative real-time reverse transcription polymerase chain reaction to observe expression levels of related genes in the skin fibroblasts. Conditions set for the instrument of the quantitative real-time reverse transcription polymerase chain reaction were: 95° C. for 20 s, 95° C. for 3 s, and 60° C. for 30 s, for 40 cycles. A 2-ΔCt method was used for gene quantification. Here, the quantitative real-time reverse transcription polymerase chain reaction on the cDNA could indirectly quantify the mRNA expression level of the gene, thereby inferring the expression level of the protein encoded by the gene.

Figure 4:
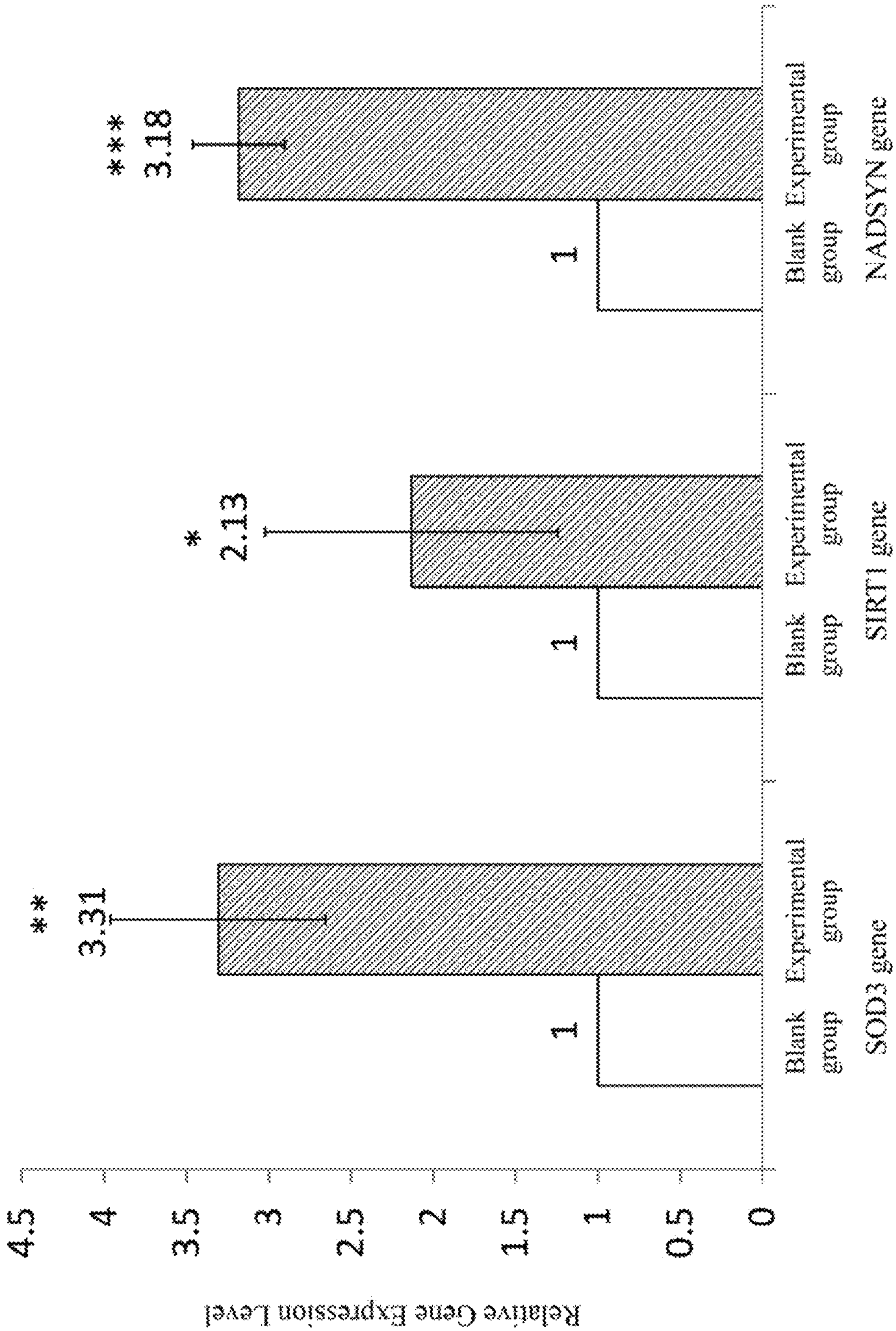
FIG. 4 is a graph showing results of a relative gene expression level test.

It should be particularly noted that the gene expression in FIG. 4 was presented in relative expression ratio. The standard deviation was calculated using a STDEV formula in software Excel, and the statistically significant difference between the groups was analyzed by student t-test. In FIG. 4, "*" represents a p-value of less than 0.05 as compared with the control group, "" represents a p-value of less than 0.01 as compared with the control group, and "*" represents a p-value of less than 0.001 as compared with the control group.

TABLE 1

| Target gene | Primer name | Sequence number | Sequence | Primer length |
|---|---|---|---|---|
| SOD3 | SOD3-F | SEQ ID NO: 1 | AGCTGGAAAGGTGCCCGA | 18 |
| | SOD3-R | SEQ ID NO: 2 | CTTGGCGTACATGTCTCGGAT | 21 |
| SIRT1 | SIRT1-F | SEQ ID NO: 3 | TGCTGGCCTAATAGAGTGGCA | 21 |
| | SIRT1-R | SEQ ID NO: 4 | CTCAGCGCCATGGAAAATGT | 20 |
| NADSYN | NADSYN-F | SEQ ID NO: 5 | GCAAAATGTGCAGGCTCGAA | 20 |
| | NADSYN-R | SEQ ID NO: 6 | GCACTGGAGCAGTCGTACTT | 20 |

In Table 1, F is a forward primer, and R is a reverse primer.

5-3 Test Results:

Referring to FIG. 4, the relative expression ratio of the SOD3 gene of the blank group was regarded as 1. Compared with the blank group, the relative expression ratio of the SOD3 gene of the experimental group was 3.31. Thus, the expression level of the SOD3 gene of the experimental group was significantly enhanced, indicating that the *Rosa canina* extract could promote production of superoxide dismutase by cells. In other words, when taken by a subject in need thereof, the *Rosa canina* extract could effectively enhance the expression level of the SOD3 gene, thereby promoting the antioxidant performance of cells.

Still referring to FIG. 4, the relative expression ratio of the SIRT1 gene of the blank group was regarded as 1. Compared with the blank group, the relative expression ratio of the SIRT1 gene of the experimental group was 2.13. Thus, the expression level of the SIRT1 gene of the experimental group was significantly enhanced. In other words, when taken by a subject in need thereof, the *Rosa canina* extract could effectively enhance the expression level of the SIRT1 gene, thereby avoiding DNA damage of cells and protein inactivation and reducing inflammatory reaction.

Still referring to FIG. 4, the relative expression ratio of the NADSYN gene of the blank group was regarded as 1. Compared with the blank group, the relative expression ratio of the NADSYN gene of the experimental group was 3.18. Thus, the expression level of the NADSYN gene of the experimental group was significantly enhanced. In other words, when taken by a subject in need thereof, the *Rosa canina* extract could effectively enhance the expression level of the NADSYN gene, thereby helping cells to synthesize NAD, so as to provide an energy source for mitochondria and maintain viability of cells.

Example 6: Test for Intestinal Ferritin Content

This test was carried out using intestinal epithelial cells to measure a ferritin content in cells, so as to test whether the absorption of iron by cells was improved.

6-1 Materials and Instruments:

Cell line: human colon cells C2BBel (ATCC® CRL-2102™).

C2BBel medium: 90% DMEM (Dulbecco's Modified Eagle Medium, Gibco) with 10% fetal bovine serum (Gibco), 1% antibiotic-antifungal agent (Gibco) and 0.01 mg/ml transferrin.

Iron-free medium: minimum essential medium (Gibco) with 10 mmol/L PIPES (filtering out NaOH to prepare a 150 mg/mL solution, filtering, and adding 1 mL of filtrate to 50 mL of medium), 4 mg/L hydrocortisone (taking 10 μL of 20 mg/ml hydrocortisone to 50 mL of medium), 5 μg Se/L sodium selenite (taking 1 μL of 250 μg/ml sodium selenite to 50 mL of medium), 34 μg/L triiodothyronine (taking 0.17 μL of 10 mg/mL triiodothyronine to 50 mL of medium), 5 mg/L insulin (taking 25 μL of 10 mg/mL insulin to 50 mL of medium), 20 μg/L epidermal growth factor (taking 10 μL of 100 mg/mL EGF to 50 mL of medium) and 1× antibiotic-antifungal agent (Gibco).

Human Ferritin (FTL) ELISA kit, purchased from Abcam.

6-2 Test Procedure:

First, initial incubation of the cells was carried out. The cells were inoculated into a 24-well plate containing 500 μL of C2BBel medium per well at a density of $2\times10^4$ per well, and cultured at 37° C. for 14 days, during which the medium was replaced every 3 days.

After the medium was removed, the cells were washed, and then incubated in the iron-free medium for 2 days.

The cells were divided into a blank group and an experimental group. For the blank group, only the iron-free medium was replaced with a fresh one. For the experimental group, not only the iron-free medium was replaced with a fresh one, but also 0.125% (m/v) of the *Rosa canina* extract prepared in Example 1 was added.

For each group, 10 μmol/mL $FeSO_4$ was added as an iron source, and incubation was carried out for 24 h. Next, after the cells of each group were collected, 200 mL of RIPA buffer was added, and the mixture was stored at −20° C. Finally, the ferritin content in cells of each group was measured with the Human Ferritin (FTL) ELISA kit.

Figure 5:
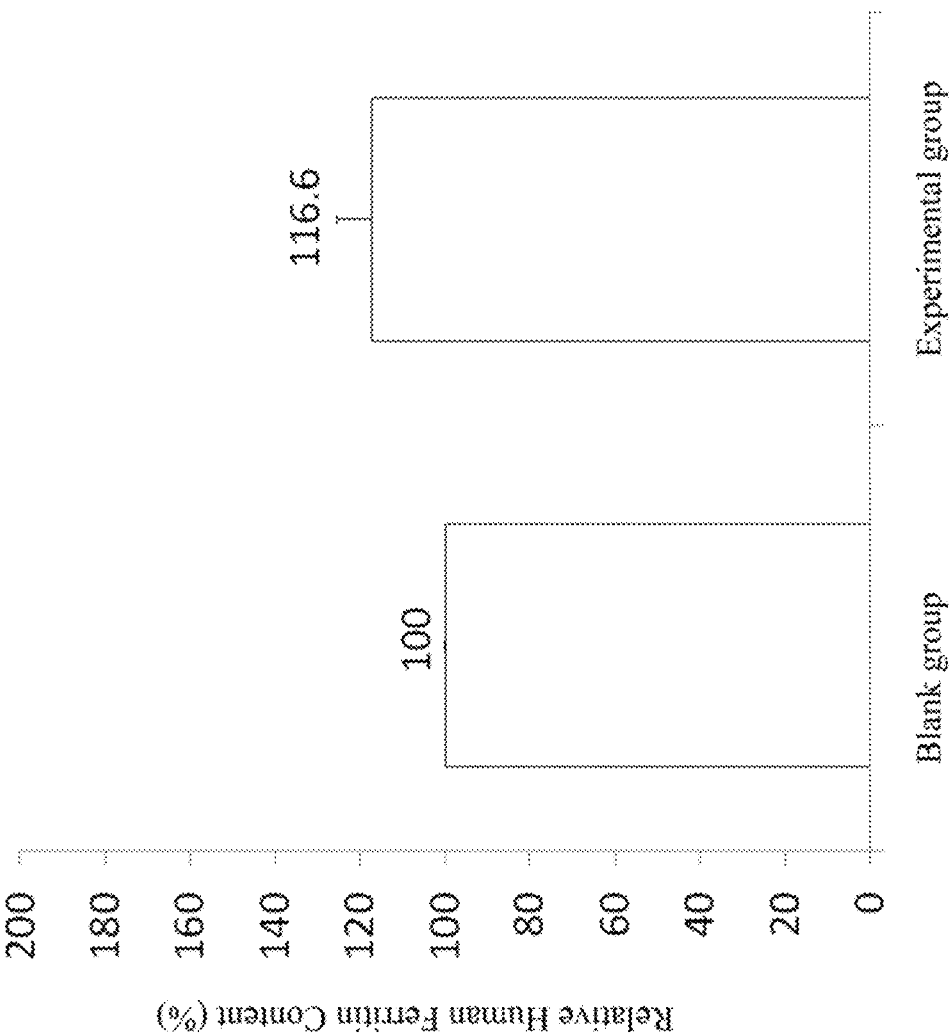
FIG. 5 is a graph showing results of a relative human ferritin content test.

6-3 Test Results:

Referring to FIG. 5, as can be known, based on the case that the ferritin content of the blank group was 100%, the ferritin content of the experimental group was 116.6%. Compared with the blank group, the ferritin content in the human colon cells of the experimental group was significantly enhanced by up to 16.6%. That is, the *Rosa canina* extract also has the effect of promoting iron absorption by the intestinal tract.

Example 7: Human Experiment

Sample: *Rosa canina* extract prepared in Example 1.

Subjects: 10 subjects. The subjects were women aged over 20 and under 65.

Generally speaking, the normal hemoglobin concentration in medicine ranges from 11.5 g/dL to 15.5 g/dL, and a hemoglobin concentration of lower than 11.5 g/dL is determined as anemia. The iron content in normal blood ranges from 50 μg/dL to 121 μg/dL, and an iron content of lower than 50 μg/dL is determined as a low iron content in blood. 6 subjects had a low hemoglobin concentration (≤11.5 g/dL) and a low iron content (<50 μg/dL) in blood.

7-1 Test Items

Items include: hemoglobin concentration, iron content in blood, skin appearance and lip color, and relative number of pores.

The hemoglobin concentration and the iron content in blood were tested using blood samples. The entrusted inspection was conducted by Le Zen Reference Lab.

Relative number of pores: facial skin of the subjects was tested using a VISIA advanced digital skin analysis system sold by Canfield, USA. The facial skin of the subjects of each group was tested for their pore expression level by a high-resolution camera lens. When the facial skin was irradiated by standard white light, the recesses at the pores on the face were shadowed, and pores appeared darker than the surrounding skin tone. In this way, the number and area of pores could be measured. Then, the pore expression level was obtained using software based on the number and area of pores. The higher the pore expression level, the larger the number and area of pores. After the analysis, taking the pore expression level of the blank group as the reference (i.e., the relative expression rate of pores on skin of the blank group was 100%), the relative expression rate of pores on skin of the experimental group was calculated.

7-2 Test Procedure:

10 subjects each took 4 g of *Rosa canina* extract daily for consecutive two weeks. The subjects were analyzed by the above-mentioned system before the intake (data on week 0 were the blank group) and after two weeks of consumption (data on week 2 were the experimental group).

Figure 6:
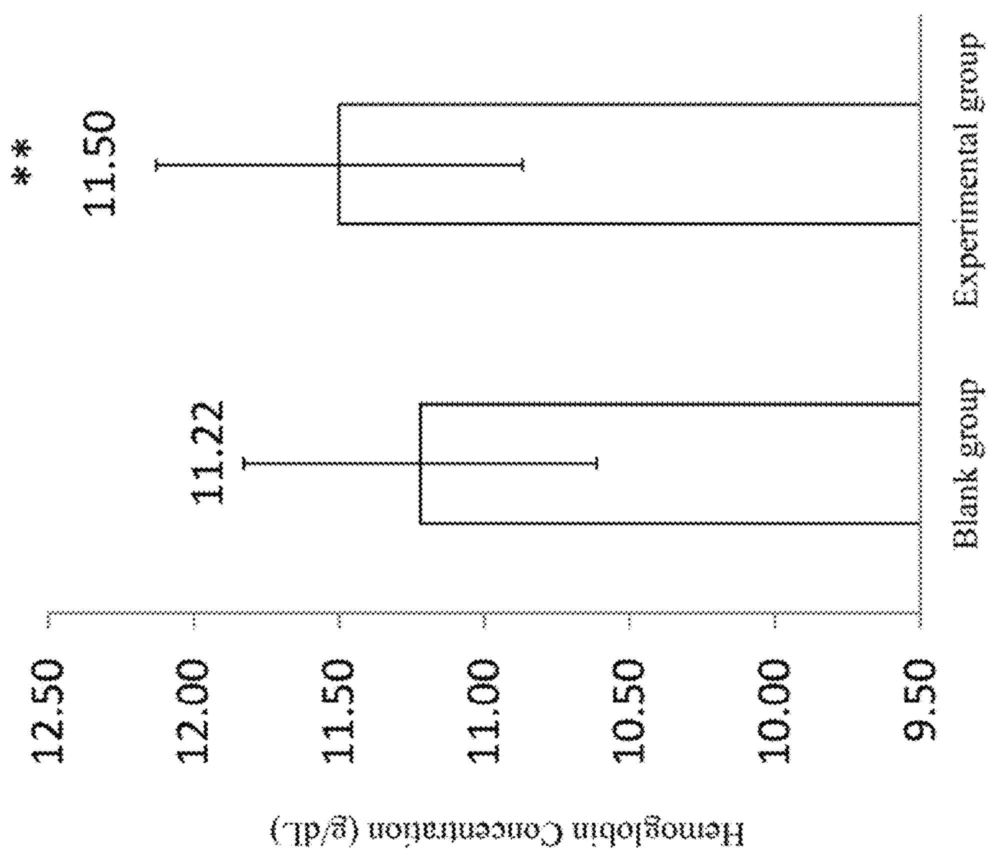
FIG. 6 is a graph showing results of hemoglobin concentrations in human experiments.

7-3 Test Results:

Referring to FIG. 6, the mean hemoglobin concentration of the blank group was 11.22 g/dL. After taking 4 g of *Rosa canina* extract daily for two weeks, the mean hemoglobin concentration of the 10 subjects was enhanced to 11.50 g/dL.

Figure 7:
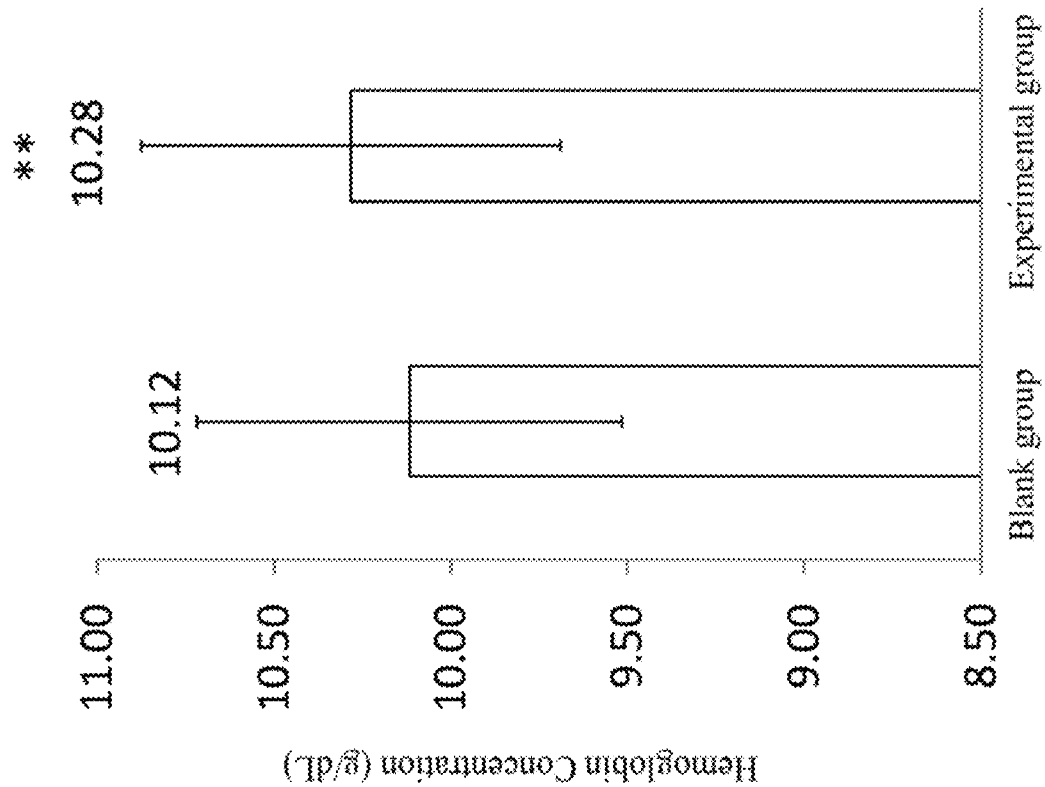
FIG. 7 is another graph showing results of hemoglobin concentrations in human experiments.

Referring to FIG. 7, 6 subjects with anemia (≤11.5 g/dL) were observed. As shown in FIG. 7, the mean hemoglobin concentration of the 6 subjects was 10.12 g/dL. After taking 4 g of *Rosa canina* extract daily for two weeks, the mean hemoglobin concentration of the 6 subjects was enhanced to 10.28 g/dL.

Figure 8:
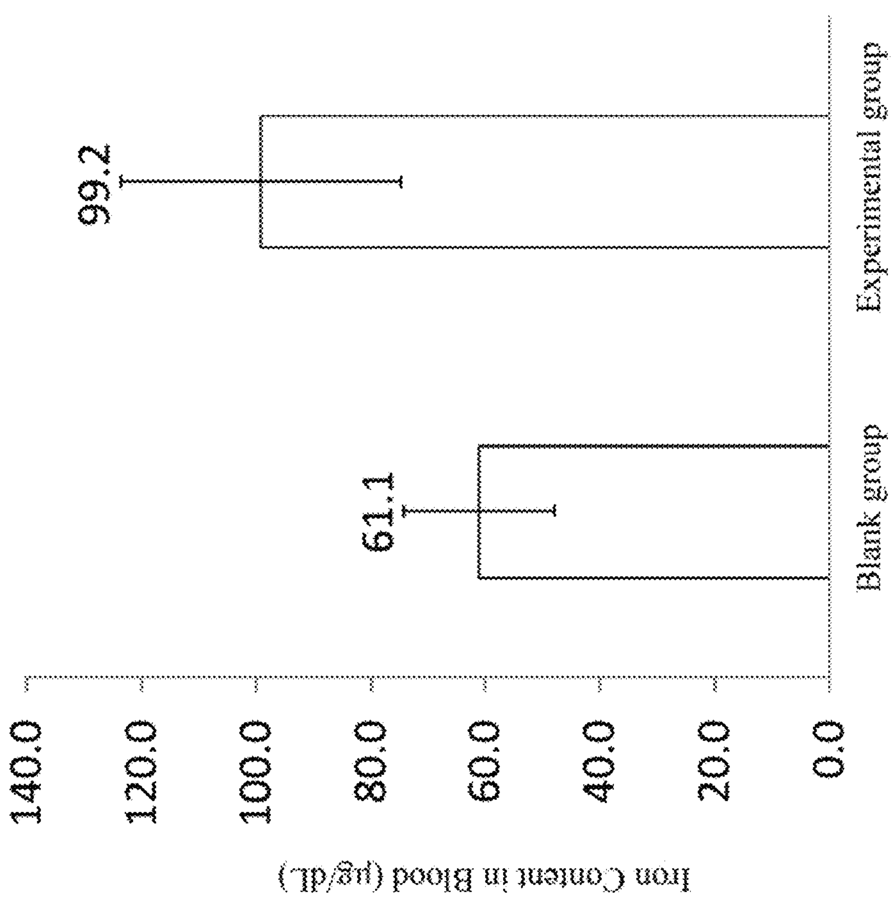
FIG. 8 is a graph showing results of iron contents in blood in human experiments.

Referring to FIG. 8, the mean iron content in blood of the blank group was 61.1 μg/dL. After taking 4 g of *Rosa canina* extract daily for two weeks, the mean iron content in blood of the 10 subjects was enhanced to 99.2 μg/dL.

Figure 9:
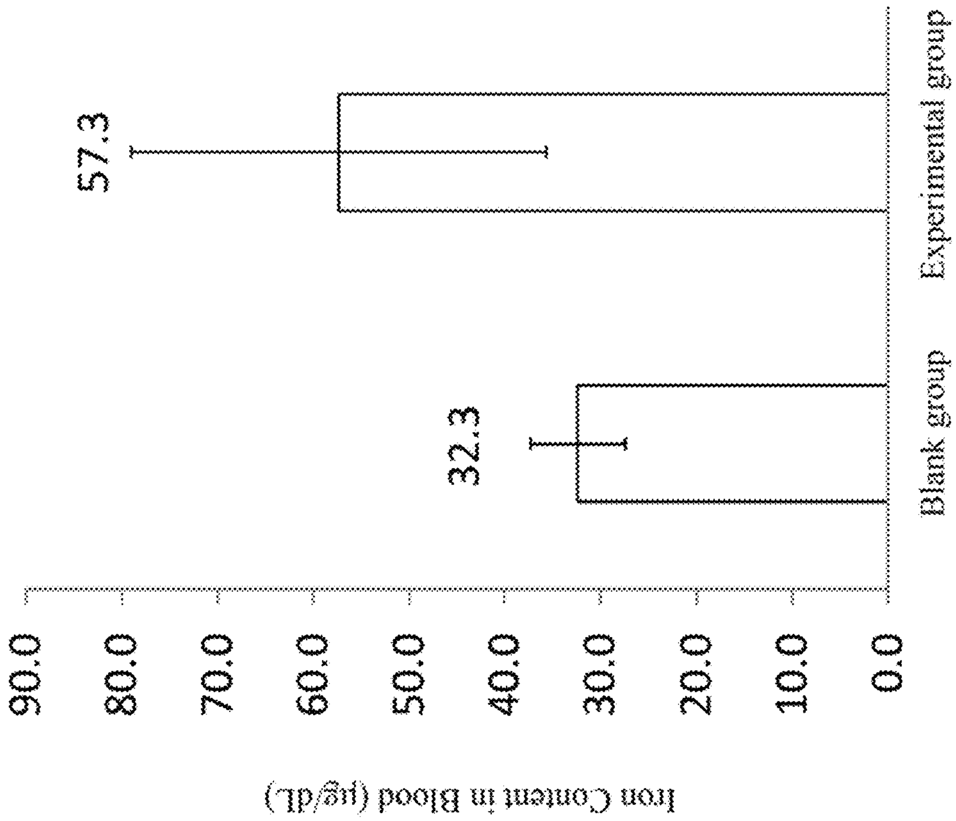
FIG. 9 is another graph showing results of iron contents in blood in human experiments.

Referring to FIG. 9, 6 subjects with anemia (<50 μg/dL) were observed. As shown in FIG. 9, the mean iron content in blood of the 6 subjects was enhanced from 32.3 μg/dL (week 0) to 57.3 μg/dL (week 2) while maintaining their daily routine. That is, after taking 4 g of *Rosa canina* extract daily for two weeks, the severely low iron content was improved back to the normal iron content range in blood in medicine of 50 μg/dL to 121 μg/dL.

Figure 10:
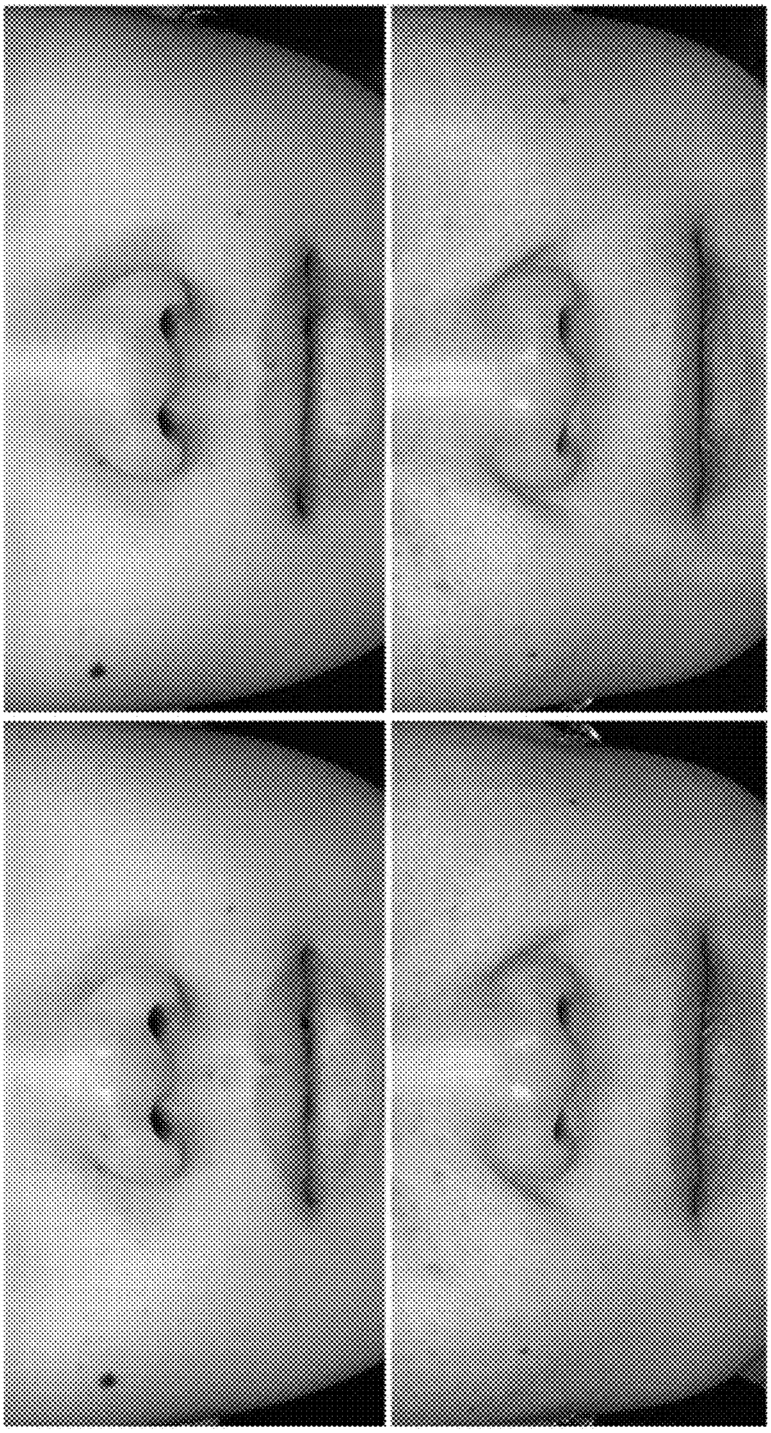
FIG. 10 shows photos showing skin appearance and lip color before and after use human experiments.

Referring to FIG. 10, taking photos of two subjects under the same light from the same angle as an example, as shown, the skin appearance and lip color of the blank group (week 0) were pale. After taking 4 g of *Rosa canina* extract daily for two weeks, it was obvious that the skin appearance and lip color of the experimental group (week 2) exhibited more ruddiness.

Figure 11:
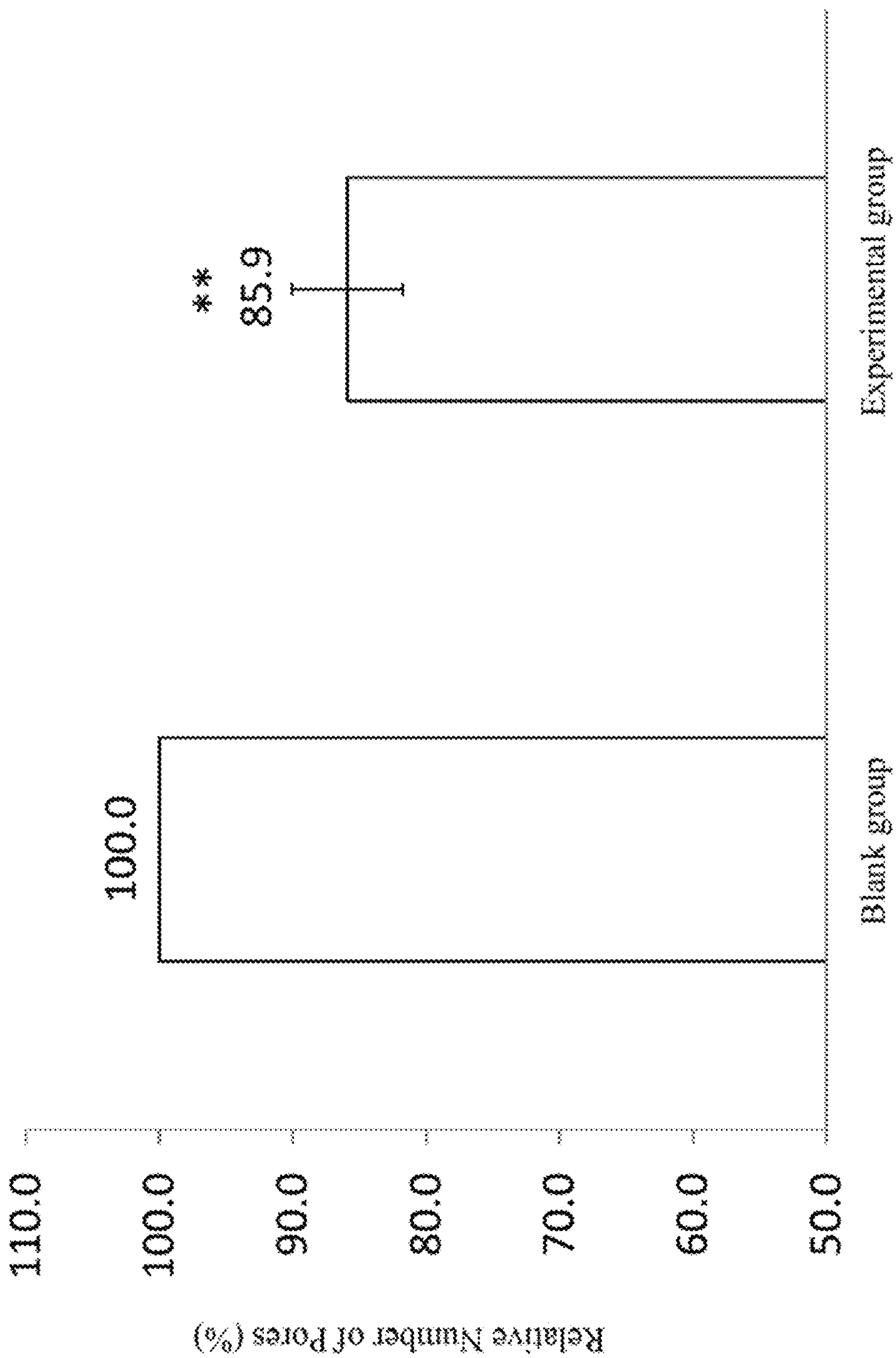
FIG. 11 is a graph showing results of relative numbers of pores in human experiments.

Referring to FIG. 11, in the case that the mean number of pores of the blank group was regarded as 100%, after taking 4 g of *Rosa canina* extract daily for two weeks of administration of the 4 g of *Rosa canina* extract daily, the mean relative number of pores of the 10 subjects was 85.9%, which was greatly reduced by 14.1%.

Based on the above, the *Rosa canina* extract according to any example can be used for preparing a composition for improving skin complexion of a subject in need thereof. The *Rosa canina* extract according to any example has at least one of the following effects: promoting iron absorption by cells, promoting hemoglobin concentration, promoting iron content in blood, promoting mitochondrial activity in cells, promoting elastin content in skin cells, enhancing antioxidant capacity of skin, and enhancing expression levels of SOD3, SIRT1 and NADSYN genes in skin fibroblasts.

Although the present disclosure has been described in considerable detail with reference to certain preferred embodiments thereof, the disclosure is not for limiting the scope of the invention. Persons having ordinary skill in the art may make various modifications and changes without departing from the scope and spirit of the disclosure. Therefore, the scope of the appended claims should not be limited to the description of the preferred embodiments described above.

What is claimed is:

1. A method for improving skin complexion of a subject in need thereof, comprising orally administering to the subject an effective dose of a *Rosa canina* extract, wherein the *Rosa canina* extract is obtained by mixing a whole fruit of *Rosa canina* by water at a weight ratio of 1:10 to obtain an extraction solution, letting the extraction solution to stay at 85° C. for 1 h, and removing solid from the extraction solution;

wherein the improvement of skin complexion is achieved by promoting cellular iron absorption, hemoglobin concentration, or blood iron content in the subject in need thereof; and the effective dose of the *Rosa canina* extract is 4 g/day.

2. The method according to claim 1, wherein the *Rosa canina* extract further promotes mitochondrial activity in cells of the subject to achieve the effect of improving skin complexion.

3. The method according to claim 1, wherein the *Rosa canina* extract further promotes elastin content in skin cells of the subject to achieve the effect of improving skin complexion.

4. The method according to claim 1, wherein the *Rosa canina* extract further enhances antioxidant capacity of skin of the subject to achieve the effect of improving skin complexion.

5. The method according to claim 1, wherein the *Rosa canina* extract further enhances expression levels of SOD3, SIRT1 and NADSYN genes in skin fibroblasts of the subject to achieve the effect of improving skin complexion.

6. The method according to claim 1, wherein the *Rosa canina* extract further reduces skin pore size of the subject to achieve the effect of improving skin complexion.

* * * * *

SEQUENCE LISTING

```
Sequence total quantity: 6
SEQ ID NO: 1            moltype = DNA  length = 18
FEATURE                 Location/Qualifiers
source                  1..18
                        mol_type = other DNA
                        organism = synthetic construct
SEQUENCE: 1
agctggaaag gtgcccga                                                  18

SEQ ID NO: 2            moltype = DNA  length = 21
FEATURE                 Location/Qualifiers
source                  1..21
                        mol_type = other DNA
                        organism = synthetic construct
SEQUENCE: 2
cttggcgtac atgtctcgga t                                              21

SEQ ID NO: 3            moltype = DNA  length = 21
FEATURE                 Location/Qualifiers
source                  1..21
                        mol_type = other DNA
                        organism = synthetic construct
SEQUENCE: 3
tgctggccta atagagtggc a                                              21

SEQ ID NO: 4            moltype = DNA  length = 20
FEATURE                 Location/Qualifiers
```

-continued

```
source                  1..20
                        mol_type = other DNA
                        organism = synthetic construct
SEQUENCE: 4
ctcagcgcca tggaaaatgt                                        20

SEQ ID NO: 5            moltype = DNA  length = 20
FEATURE                 Location/Qualifiers
source                  1..20
                        mol_type = other DNA
                        organism = synthetic construct
SEQUENCE: 5
gcaaaatgtg caggctcgaa                                        20

SEQ ID NO: 6            moltype = DNA  length = 20
FEATURE                 Location/Qualifiers
source                  1..20
                        mol_type = other DNA
                        organism = synthetic construct
SEQUENCE: 6
gcactggagc agtcgtactt                                        20
```